United States Patent [19]
Borchert et al.

[11] Patent Number: 6,129,682
[45] Date of Patent: Oct. 10, 2000

[54] NON-INVASIVE METHOD OF MEASURING CEREBRAL SPINAL FLUID PRESSURE

[75] Inventors: Mark S. Borchert, La Canada; James L. Lambert, Sunland, both of Calif.

[73] Assignee: California Institute of Technology, Pasadena, Calif.

[21] Appl. No.: 09/021,966

[22] Filed: Feb. 11, 1998

Related U.S. Application Data

[60] Provisional application No. 60/037,713, Feb. 12, 1997.

[51] Int. Cl.$^7$ ........................................................ A01B 5/00

[52] U.S. Cl. ............................................ 600/561; 600/486

[58] Field of Search ...................................... 600/561, 486

[56] References Cited

U.S. PATENT DOCUMENTS

| | | |
|---|---|---|
| 3,929,124 | 12/1975 | Yablonski et al. . |
| 5,005,577 | 4/1991 | Frenkel ..................................... 600/561 |
| 5,065,767 | 11/1991 | Maddess . |
| 5,143,080 | 9/1992 | York ........................................ 600/561 |
| 5,291,899 | 3/1994 | Watanabe et al. ........................ 600/561 |
| 5,439,441 | 8/1995 | Grimsley et al. ........................ 600/561 |

*Primary Examiner*—Cary O'Connor
*Assistant Examiner*—Pamela L. Wingood
*Attorney, Agent, or Firm*—Fish & Richardson P.C.

[57] ABSTRACT

The invention provides a method of non-invasively determining intracranial pressure from measurements of an eye. A parameter of an optic nerve of the eye is determined, along with an intraocular pressure of the eye. The intracranial pressure may be determined from the intraocular pressure and the parameter.

21 Claims, 3 Drawing Sheets

NON-INVASIVE METHOD OF MEASURING CEREBRAL SPINAL FLUID PRESSURE

CROSS REFERENCE TO RELATED APPLICATIONS

This application is a continuation-in-part of U.S. Provisional Application Ser. No. 60/037,713 Filed Feb. 2, 1997, the entirety of which is incorporated by reference herein.

STATEMENT AS TO FEDERALLY SPONSORED RESEARCH

The invention described herein was made in the performance of work under a NASA contract, and is subject to the provisions of Public Law 96-517 (35 U.S.C. 202) in which the Contractor has elected to retain title.

BACKGROUND AND SUMMARY OF THE INVENTION

Intracranial pressure ("ICP") is usually approximated by the cerebral spinal fluid ("CSF") pressure. CSF pressure is usually measured by means of a spinal tap which involves puncturing the subarachnoid space of the spinal cord. For numerous diseases this must be done repeatedly to monitor treatment results or disease progression. Such invasive monitoring is associated with risk and discomfort and is not always feasible.

The invention allows measurement of the ICP to be made in a simpler and far less painful way than prior methods. This type of measurement would be non-invasive and would not involve a spinal tap. In fact, the patient may simply look into a retinal scanner in order to allow the measurement to be taken. This invention can be used to measure ICP in patients or environments where other techniques of ICP measurement are not feasible or practical, such as during space flight.

The invention takes advantage of the fact that ICP may be sensed from appropriate measurements of portions of the eye. In particular, and referring to FIG. 1 (A), the sclera 16 is a firm fibrous membrane that serves to maintain the form of the eye globe and does not change with changes in intraocular pressure. The choroid 18 is a thin, vascular layer which covers the posterior five-sixths of the globe. Choroid 18 is pierced behind by an optic nerve 12 which is covered by a nerve sheath 14. The optic nerve sheath is fibrous, inelastic and continuous with the sclera of the eye and the dural covering of the brain. Choroid 18 is fixed to sclera 16. The inner surface of choroid 18 is covered by retina 22. A thin cribriform lamina (the lamina cribrosa) is formed at the point where optic nerve 12 passes through sclera 16. The minute orifices in this region serve for the passage of nerve fibers.(see FIG. 1 (B).

The intracranial pressure and pressure within the optic nerve sheath have been shown to be approximately equal. In cadaveric studies, the optic nerve pressure changes almost immediately with changes in ICP. The relationship of optic nerve pressure to ICP has been shown to be substantially linear (essentially 1:1) with optic nerve pressure being generally slightly less than ICP.

The intraocular pressure ("IOP") is higher than the ICP under normal circumstances (e.g., IOP:12–20 mm Hg supine; ICP:7–14 mm Hg supine; ICP:0–2 mm Hg standing). IOP and ICP transmit hydrostatic forces to opposite sides of the lamina cribrosa (also referred to as the scleral canal). Both blood flow and axoplasmic flow through the lamina cribrosa may be restricted in proportion to the amount of differential pressure. Exposure to such differential pressures can bow the lamina cribrosa anteriorly if ICP>IOP, or posteriorly if ICP<IOP, producing the clinical conditions of papilledema and glaucoma, respectively. Measurement of changes in the anterior-posterior position of the optic nerve head relative to a fixed structure such as the sclera or choroid, while simultaneously measuring intraocular pressure, allows for calculation of intracranial pressure.

Prolonged ICP>IOP results in papilledema. Papilledema describes the ophthalmoscopic appearance of the optic nerve head when the axons of the optic nerve head and retinal nerve fiber layer ("NFL") become swollen from restricted axoplasmic flow. There may be a twenty-fold thickening of the nerve fibers under such circumstances. Papilledema only occurs when there is patency between the subarachnoid spaces of the optic nerve and the brain, so that ICP can be transmitted to the optic nerve.

Ophthalmoscopically visible papilledema can be seen within 2–4 hours of onset of highly elevated ICP. Sensitive techniques for measurement of NFL thickness in the retina or optic nerve head may detect early papilledema before it becomes visible with the ophthalmoscope. Measurement of NFL thickness with simultaneous measurment of IOP would also permit calculation of ICP.

Optical coherence tomography ("OCT")is a technique which may be used to monitor the early morphologic changes of the optic nerve head associated with changes in ICP or IOP quantifiably. It avoids the vagaries introduced by processing and interpretation of prior techniques such as color fundus photography. In addition, OCT can detect axonal swelling earlier than other imaging techniques (e.g., stereoscopic fundus photography, optic nerve head analyzers, ophthalmoscopy) because these techniques depend upon changes in surface topography.

OCT can measure NFL thickness or relative anterior-posterior position of the optic nerve head regardless of changes in surface topography.

Refinement of OCT to study ICP may in addition lead to the ability to measure other systemic or intraocular parameters non-invasively. For instance, measurements of retinal blood flow with OCT Doppler techniques can be used to study indices such as pH or pCO2 when other parameters which control retinal blood flow are known.

BRIEF DESCRIPTION OF THE DRAWINGS

FIG. 1 (B) is a scanning electron micrograph of the lamina cribrosa demonstrating hundreds of trabecular channels through which optic nerve axons pass.

DESCRIPTION OF THE PREFERRED EMBODIMENTS

The invention involves measuring the thickness of the NFL, anterior-posterior position of the optic nerve head, or other parameters, and correlating the same with ICP pressure. The invention employs an imaging scan and IOP measurements.

The imaging scan may be performed by an technique sensitive enough to detect changes in ocular parameters, such as by OCT. OCT utilizes a scanning fiber interferometer to image tissue in cross-section at high resolution (2–30 μm). An FDA-approved OCT scanner, with 12 μm resolution, is available for non-invasively scanning the human retina from, e.g., Humphrey Instruments. OCT may be employed to accurately measure morphological changes which occur due to IOP and ICP transmitting hydrostatic forces to opposite sides of the lamina cribrosa.

In OCT, a beam of light is scanned across tissue and the reflected light is collected by a detector. Only the light which is reflected from a site within the tissue that is equidistant in optical path length from the detector as is an oscillating mirror contributes to the image.

Any tissue through which light can be transmitted can be sectioned optically. In the retina, details of histologic layers from the NFL on the surface down to the sclera can be seen in vivo. Details of the OCT technique may be found in *OCT of Ocular Diseases*, by Carmen A. Puliafito, Michael Hee, Joel Schuman, and James Fujimoto, published 1996 by SLACK, Thorofare, N. J., and incorporated herein by reference.

Figure 1A:
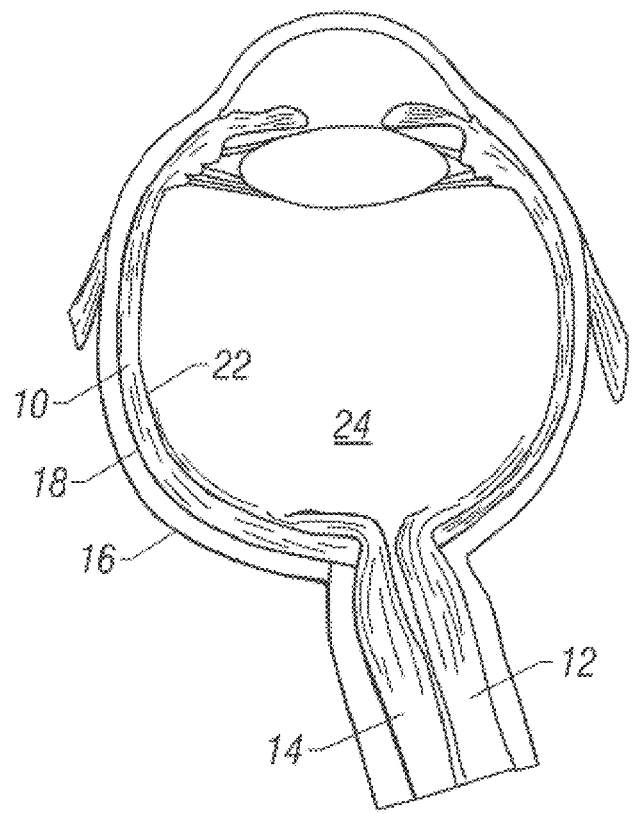
FIG. 1 (A) is a diagram of a horizontal section of an eye.
Figure 1B:
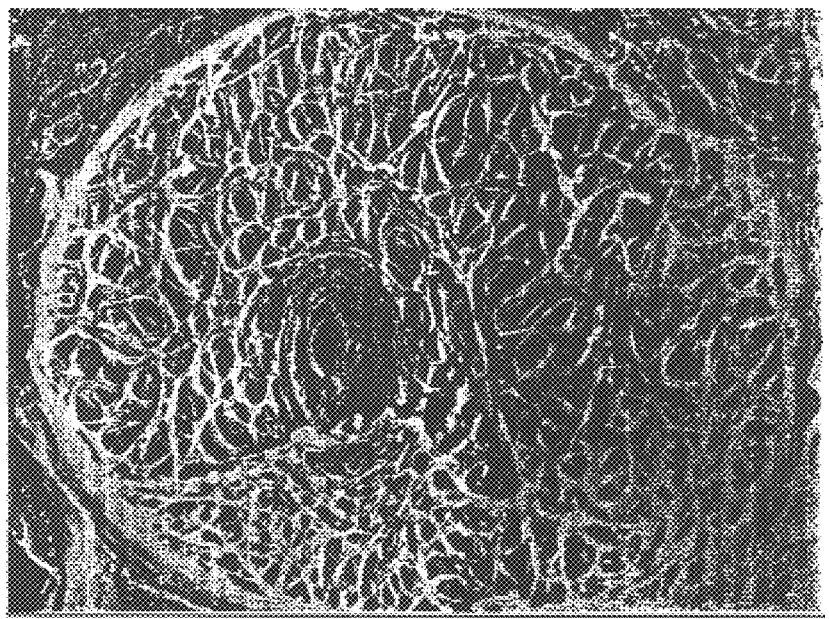
Figure 2:
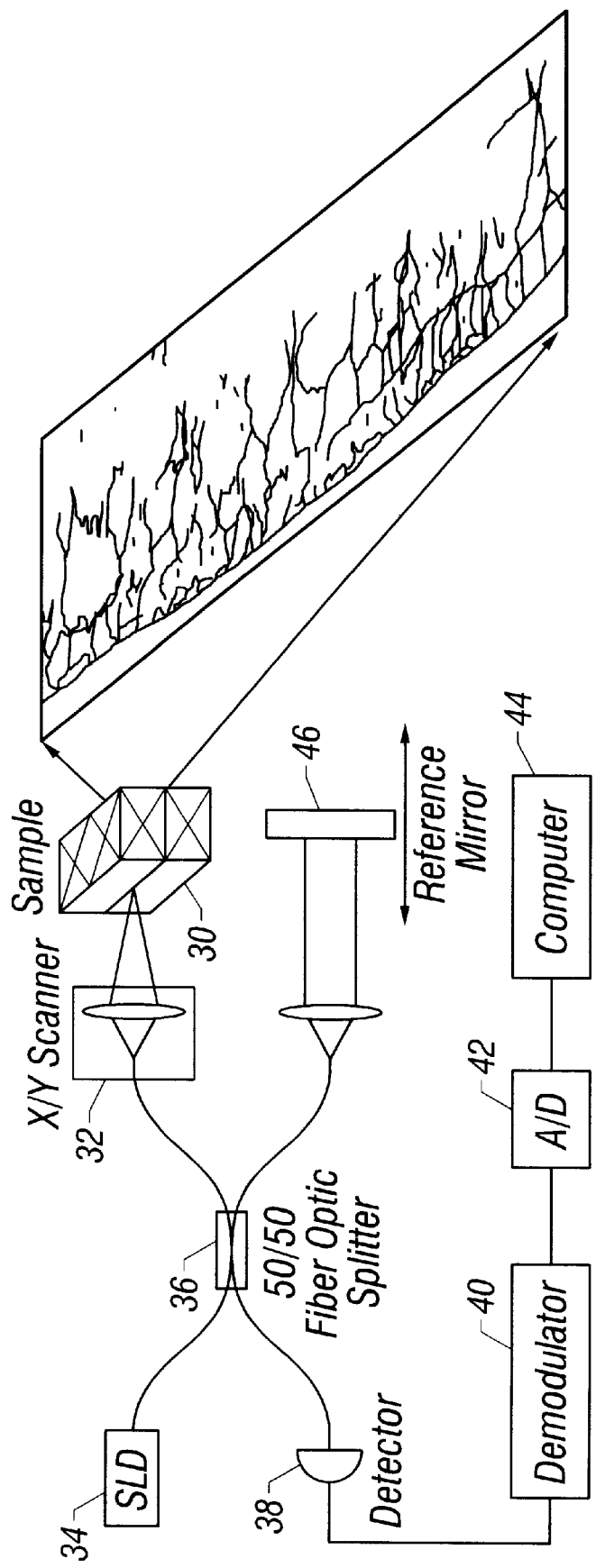
FIG. 2 shows an OCT system which utilizes low coherence interferometry to measure the reflectivity of a semitransparent sample.

Referring to FIG. 2, a sample 30 is examined by an x-y scanner 32. Illumination is provided by a super luminescent diode 34 through a 50/50 fiber optic splitter 36. Splitter 36 also illuminates an oscillating mirror 46. The collected light from mirror 46 and sample 30 is sent to a detector 38 and from there to a demodulator 40, an A/D converter 42, and a computer 44.

The OCT device has a resolution of about 10–12 μm. By way of comparison, another device which measures subsurface parameters, the confocal scanning laser ophthalmoscope, has a resolution of about 500 μm.

OCT is useful in this application because the deformation associated with the displacement of the lamina cribrosa due to the tissue pressure differences across the lamina cribrosa causes relative blockage of axoplasmic flow and consequent swelling of the NFL of the optic disc and surrounding retina. Congestion of the laminar spaces with swollen axons results in partial obstruction of venous outflow and consequent hyperemia of the optic disc. The amount of swelling of the NFL of the retina and the speed of that swelling is related to the difference between the ICP and the IOP.

These phenomena can be measured with OCT because the technique can visualize deep and surface topographic changes of the optic disc. OCT may also be used to visualize venous and arterial blood flow and shifts in the spectral reflectance characteristics of the optic disc. An approximation of the ICP can be made non-invasively in humans by monitoring changes of the optic nerve head with OCT while measuring IOP.

Early swelling of the nerve fibers or forward displacement of the optic disc indicates that the subarachnoid pressure of the optic nerve (and hence the ICP) has exceeded the IOP. These changes in the optic nerve head would not be expected even in the presence of elevated ICP if the IOP is elevated. However, the anterior-posterior position of the optic nerve head or the NFL thickness can still be used to calculate the ICP if the IOP is known.

OCT is used to determine the time-dependent and statistical relationship between the thickening of the NFL and the bowing of the lamina cribrosa to exposure of differential ICP and IOP pressure. The ICP is determined from OCT-acquired retinal parameters with a known IOP.

Software is used to analyze the measured OCT-acquired data including NFL thickness and total sensory retina thickness between the well-defined reflectance peaks at the internal limiting membrane and retinal pigment epithelium ("RPE"). Appropriate software can measure NFL thicknesses with less than 3 μm variation (about 10%) in normal individuals at any specific retinal location. Changes in NFL thickness as measured by this technique can clearly distinguish patients with early NFL thinning due to glaucoma.

Figure 3:
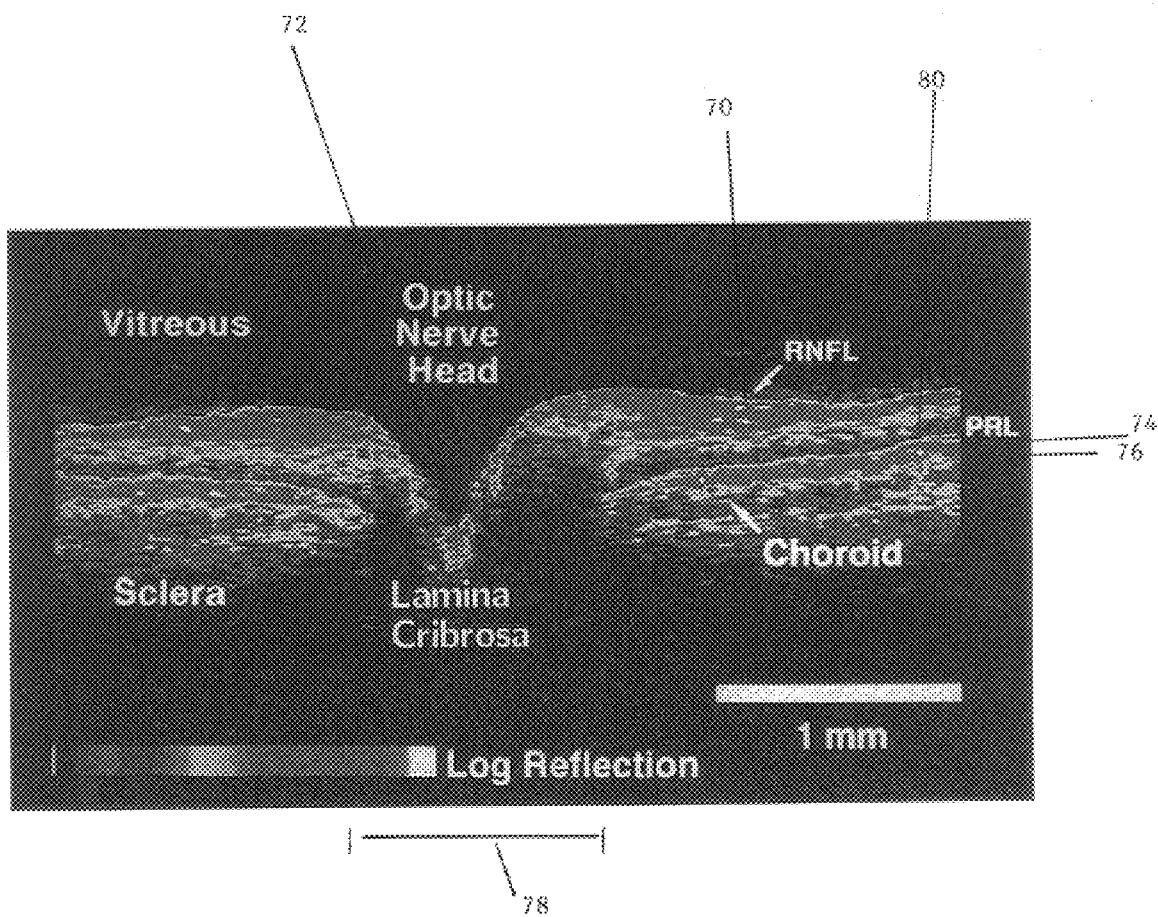
FIG. 3 shows an OCT image revealing layers of a retina (from *OCT of Ocular Diseases*, by Carmen A. Puliafito, Michael Hee, Joel Schuman, and James Fujimoto, published 1996 by SLACK).

The OCT scanner achieves registration of retinal layers by filtering out variations in the axial or longitudinal position of the eye, where the axis is from the center of the pupil to the back of the retina. Referring to FIG. 3, the OCT generates a subsurface reflectance image along the scan-line revealing layers of the retina. The NFL thickness (in FIG. 3, the retinal NFL (RNFL) 70) diminishes with distance from a nerve head 72. FIG. 3 also shows the position of the photoreceptor layer PRL 78.

The landmark for determining the optic disc relative position may be the high reflectance signal generated at the position of RPE 74 shown as the top surface of the choroid 76. The average position of this signal, closest to the optic nerve head on each side, defines this landmark. The distance between this location on each side measures the diameter of the optic nerve head which may be identified with the optic disc diameter 78. The line between these points defines the fixed baseline in the anterior-posterior axis. Anterior-posterior coordinates for every pixel of interest in this region is determined relative to this baseline.

In different individuals, the distance the optic nerve head moves with IOP and ICP may vary with the diameter of the optic disc 78. In other words, the mean position of the surface of the optic disc is dependent on the size of the optic cup, which in normal individuals is dependent upon the size of the optic disc, and the disc diameter may be factored into the analysis.

An abrupt change in reflectance defines the anterior and posterior boundaries of the optic disc. The anterior boundary represents the surface of the optic disc. The posterior boundary represents the lamina cribrosa. The positions of the maximum and minimum points of these boundaries may be studied relative to the baseline established by the signal from the RPE. The mean anterior-posterior position of these boundaries may then be measured.

In order to determine the optimum optic nerve head parameters for measuring ICP, subjects undergoing ICP monitoring by other techniques may undergo simultaneous measurements of IOP using standard ocular tonometry. Multiple OCT scans can be acquired in each subject. These scans may be circular, linear, or another shape. Each scan may be repeated to test for intra subject variability. These scans provide information on: NFL thickness in locations where the thickness in healthy subjects is already known; NFL thickness at the inferior and superior poles of the optic disc where swelling is reported to first occur in papilledema; relative anterior-posterior position of the optic nerve head; and diameter of the optic disc. The diameter of the optic disc is important as it may affect the displacement of the lamina cribrosa as a function of translaminar pressure. These parameters may be analyzed individually and as multiple variables for correlation with differences between ICP and IOP. For example, one combination of multiple variables which may be examined for correlations includes the diameter of the optic disc, the NFL thickness, and the relative anterior-posterior position.

The imaging scan allows measurement of optic nerve parameters such as thickness, position, etc. The relative position may be measured with respect to a fixed structure in the back of the eye, such as the RPE layer or the choroid layer, which generally do not shift with changes in IOP or ICP. The optic nerve parameters change with ICP and IOP. The IOP can be measured in a known manner. The relationship between the ICP and the optic nerve parameters can be determined by a correlation of the ICP and optic nerve parameters in a number of test subjects. A known "normal" ICP for a given individual may be used if available for even greater precision. The ICP may then be determined from a knowledge of the optic nerve parameters as determined by the imaging scan, and taking into account the IOP.

In another embodiment of the invention, a measurement of a movement or compliance of the anterior-posterior position of the optic nerve head may proceed simultaneously with a measurement of, and controlled changes in, the IOP. For example, an OCT may measure the position of the optic nerve head and standard tonometry may measure the IOP. A known pressure is then applied to the globe either with the tonometer or some other device to displace the optic nerve head posteriorly. This new position of the optic nerve head is measured with OCT. The compliance of the optic nerve head with changes in the IOP may then be determined. From this knowledge, a correlation may be made to the ICP.

For example, the characteristic bowing of a lamina cribrosa (as visible by OCT) may be known for a "normal" patient and in this case the ICP would be approximately equal to IOP. If a patient has ICP>IOP, the characteristic bowing is altered and may be observed by OCT. A pressure applied to the eye would tend to bow the lamina cribrosa back towards its "normal" position. Once the lamina cribrosa is at its normal position, the ICP may be identified as equal to the sum of the IOP, previously measured, and the applied pressure.

Modification of the instrument may be performed to further increase the sensitivity of the instrument to detecting changes in ICP. E.g., using an ultrafast pulsed laser instead of a superluminescent diode as a light source has resulted in a ten-fold improvement in resolution. Hardware and software modifications permit simultaneous optical Doppler imaging for precise measurement of blood flow within individual small blood vessels. Finally, shifts in the spectral reflectance characteristics of the optic disc with axon swelling, vascular engorgement, oxygen saturation, or ischemic changes could be detected.

Variations caused by motion artifacts are problematic because the scan position cycle time of approximately one second is similar to the cardiac interbeat duration. Consequently, a motion artifact induced by one cardiac pulse is completely embedded in each scan. The normal longitudinal variability in the reflectance may be determined for specific retinal points averaged over many scans both with and without a filtering mechanism. If the variability is unacceptable, the control software may be modified to reduce motion artifacts, particularly those induced by cardiac pulsations. E.g., the scan cycle time may be reduced from one second to 100 msec by acquiring only every tenth longitudinal position with each scan cycle (i.e. interleaving by a factor of 10). This completely separates motion artifacts of greater than 100 msec periodicity from the scans. The scans may then be longitudinally re-aligned and interleaved to form a composite image with motion artifacts filtered out. Single and multiple variables, defining the relative position of the optic disc may be explored using the OCT scan after reducing variability in the longitudinal signal.

It should be noted that the imaging device may be any which is capable of detecting appropriate changes in eye features. For example, ultrasound may be used instead of an OCT. Stereophotography may be used, of the type used in optic nerve head analyzers, if the changes in eye features with ICP and IOP are primarily on the surface of the optic nerve head.

While the invention has been described with respect to a number of embodiments, those of ordinary skill in the art will recognize that variations may also be envisioned. All studies may be performed in human subjects and/or a variety of animal models and in both the living and post-mortem states. Thus, the scope of the invention is limited only by the claims appended hereto.

What is claimed is:

1. A method of non-invasively determining intracranial pressure from measurements of an eye, comprising the steps of:
   (A) determining a parameter of an optic nerve of the eye;
   (B) determining an intraocular pressure of the eye; and
   (C) correlating the parameter and the intraocular pressure with intracranial pressure.

2. The method of claim 1, wherein the determining step includes the step of performing a scan across a section of the optic nerve or adjacent retina.

3. The method of claim 2, wherein the scan is performed by optical coherence tomography.

4. The method of claim 2, wherein the scan is performed across the thickness of the optic nerve.

5. The method of claim 1, wherein the parameter is thickness.

6. The method of claim 1, further comprising the step of determining a relationship between an optic nerve parameter at a predetermined position and intracranial pressure.

7. The method of claim 6, wherein the predetermined location includes at least one of: an inferior or superior pole of an optic disc, a relative anterior-posterior position of the optic disc, or a diameter of the optic disc.

8. The method of claim 2, wherein the scan is performed across the optic nerve head.

9. The method of claim 2, wherein the scan is linear.

10. The method of claim 2, wherein the scan is circular.

11. The method of claim 2, wherein the scan is performed by ultrasound.

12. The method of claim 1, wherein the parameter is nerve fiber layer thickness.

13. The method of claim 1, wherein the parameter is a relative anterior-posterior position of the optic nerve head.

14. The method of claim 13, wherein the position is an average position of a surface.

15. The method of claim 13, wherein the position is a position of extremal reflectance.

16. The method of claim 13, wherein the position measured with respect to a fixed structure in the eye.

17. The method of claim 16, wherein the structure is an RPE layer.

18. The method of claim 16, wherein the structure is a choroid layer.

19. A method of non-invasively determining intracranial pressure from measurements of an eye, comprising the steps of:
   (A) determining a set of parameters of an optic nerve of the eye, the set including at least two of the set including a diameter of an optic disc, a nerve fiber layer thickness, and a relative anterior-posterior position of an optic nerve head;
   (B) determining an intraocular pressure of the eye; and
   (C) correlating the set of parameters and the intraocular pressure with intracranial pressure.

20. The method of claim 19, wherein the correlation between the set of parameters and the intraocular pressure is a linear combination.

21. The method of claim 19, wherein the correlation between the set of parameters and the intraocular pressure is a nonlinear combination.

* * * * *